United States Patent [19]

Dellaria et al.

[11] Patent Number: 5,446,062
[45] Date of Patent: Aug. 29, 1995

[54] ((4-ALKOXYPYRAN-4-YL) SUBSTITUTED) ETHER, ARYLALKYL-, ARYLALKENYL-, AND ARYLALKYNYL)UREA INHIBITORS OF 5-LIPOXYGENASE

[75] Inventors: Joseph F. Dellaria, Lindenhurst; Anwer Basha, Lake Forest; Lawrence A. Black, Vernon Hills; Linda J. Chernesky, Arlington Heights; Wendy Lee, Chicago, all of Ill.

[73] Assignee: Abbott Laboratories, Abbott Park, Ill.

[21] Appl. No.: 152,569

[22] Filed: Nov. 12, 1993

[51] Int. Cl.$^6$ .................. A61K 31/35; C07D 309/10; C07D 405/10
[52] U.S. Cl. .................. 514/459; 514/330; 514/255; 514/231.5; 514/227.8; 544/374; 544/149; 544/58.4; 546/207; 549/416; 549/419; 549/420
[58] Field of Search .......... 549/416, 419, 420; 548/318; 544/318, 317, 149, 58.4, 374; 514/459, 422, 256, 330, 255, 231.5, 227.8; 546/207

[56] References Cited

FOREIGN PATENT DOCUMENTS

| 0375404 | 6/1990 | European Pat. Off. ... C07D 309/10 |
| 0375457 | 8/1990 | European Pat. Off. ... C07D 317/22 |
| 0385662 | 9/1990 | European Pat. Off. ... C07D 405/12 |
| 0385663 | 9/1990 | European Pat. Off. ... C07D 215/22 |
| 0409412 | 1/1991 | European Pat. Off. ... C07D 317/18 |
| 0462812 | 12/1991 | European Pat. Off. ... C07D 409/04 |

OTHER PUBLICATIONS

C. Crawley, et al., *J. Med. Chem.*, 1992, 35, 2600–2609.

*Primary Examiner*—Nicky Chan
*Attorney, Agent, or Firm*—Jerry F. Janssen

[57] ABSTRACT

Compounds of the structure

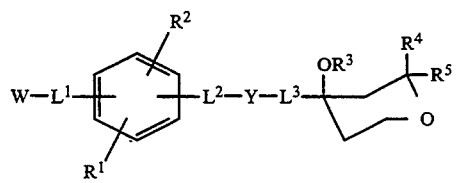

where W is selected from

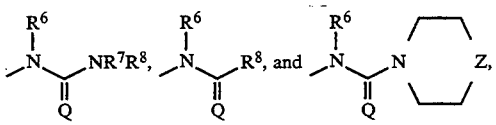

where Q is oxygen or sulfur, $R^6$ and $R^7$ are hydrogen or alkyl, or $R^6$ and $R^7$, together with the nitrogen atoms to which they are attached, define a radical of formula

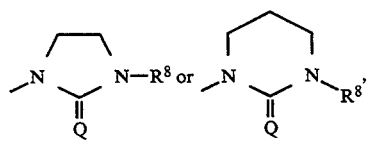

Z is —$CH_2$—, oxygen, sulfur, or —$NR^9$, $L^1$ and $L^2$ are selected from a valence bond, alkylene, propenylene, and propynylene; $R^1$ and $R^2$ are independently selected from alkyl, alkoxy, haloalkyl, halogen, cyano, amino, alkoxycarbonyl, and dialkylaminocarbonyl; Y is selected from oxygen, >$NR^{10}$, and

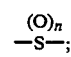

$L^3$ is selected from alkylene of one to three carbon atoms, propenylene, propynylene,

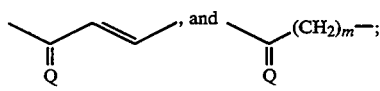

and $R^3$, $R^4$, and $R^5$ are hydrogen or alkyl of one to four carbon atoms inhibit the synthesis of leukotrienes. These compounds are useful in the treatment or amelioration of allergic and inflammatory disease states.

6 Claims, No Drawings

((4-ALKOXYPYRAN-4-YL) SUBSTITUTED) ETHER, ARYLALKYL-, ARYLALKENYL-, AND ARYLALKYNYL)UREA INHIBITORS OF 5-LIPOXYGENASE

TECHNICAL FIELD

This invention relates to compounds having biological activity to inhibit lipoxygenase enzymes, to pharmaceutical compositions comprising these This invention relates to compounds having biological activity to inhibit lipoxygenase enzymes, to pharmaceutical compositions comprising those compounds, and to a medical method of treatment. More particularly, this invention concerns certain ((4-alkoxypyran-4-yl)-substituted) ether, sulfide, sulfone, and sulfoxide arylalkyl-, arylalkenyl-, and arylalkynyhrea compounds which inhibit leuko-triene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, convening them to 1-hydroperoxy -trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to LTA$_4$. This reactive leukotriene intermediate is enzymatically hydrated to LTB$_4$ or conjugated to the tripepride glutathione to produce LTC$_4$. LTA$_4$ can also be hydrolyzed nonenzymatically to form two isomers of LTB$_4$. Successive proteolytic cleavage steps convert LTC$_4$ to LTD$_4$ and LTE$_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the fast step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain triether compounds which inhibit lipoxygenase enzyme activity and are useful in the treatment of allergic and inflammatory disease states in which leukotrienes play a role.

The compounds of this invention and the pharmaceutically acceptable salts thereof have the structure

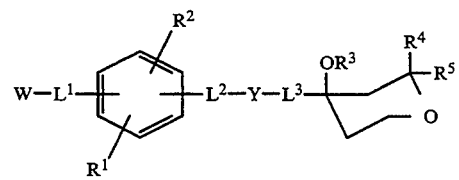

where W is selected from

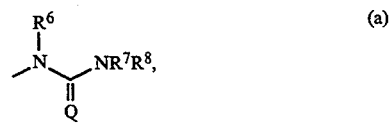  (a)

  (b)

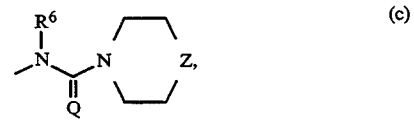  (c)

where Q is oxygen or sulfur, $R^6$ and $R^7$ are independently selected from hydrogen and alkyl of one to four carbon atoms, provided that when $L^1$ is a valence bond, $R^6$ is alkyl of one to four carbon atoms, or $R^6$ and $R^7$, together with the nitrogen atoms to which they are attached, define a radical of formula

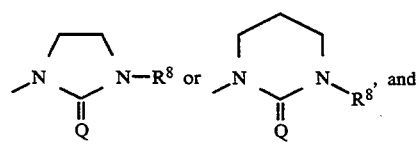

$R^8$ is selected from the group consisting of (a) hydrogen, (b) alkyl of one to four carbon atoms, (c) haloalkyl of one to four carbon atoms, (d) cyanoalkyl of one to four carbon atoms, (e) carboxyalkyl of from two to four carbon atoms, (f) (alkoxycarbonyl)alkyl where the alkyl and alkoxy portions each are of one to four carbon atoms, (g) (alkylaminocarbonyl)alkyl, where the alkyl and aminoalkyl portions each are of one to four carbon atoms, and (h) phenyl, optionally substituted with alkyl of one to four carbon atoms, alkoxy of one to four carbon atoms, haloalkyl, or halogen, hydroxyalkyl of from one to four carbon atoms, aminoalkyl of from one to four carbon atoms, carboxyalkyl of from two to four carbon atoms, (alkoxycarbonyl)alkyl where the alkyl and alkoxy portions each are of one to four carbon atoms, or (alkylaminocarbonyl)alkyl, where the alkyl and aminoalkyl portions each are of one to four carbon atoms.

The group Z is $-CH_2-$, oxygen, sulfur, or $-NR^9$ where $R^9$ is hydrogen or alkyl of one to four carbon atoms.

$L^1$ is a valence bond or is selected from alkylene of one to three carbon atoms, propenylene, and propynylene, $R^1$ and $R^2$ are independently selected from alkyl of one to four carbon atoms, alkoxy of one to four carbon atoms, haloalkyl, halogen, cyano, amino, alkylamino of one to four carbon atoms, dialkylamino where the two alkyl groups are independently of one to four carbon atoms, carboxyl, alkoxycarbonyl of one to four carbon atoms, and dialkylaminocarbonyl where the alkyl portions are each of one to four carbon atoms.

$L^2$ is a valence bond or is selected from alkylene of one to three carbon atoms, propenylene, and propynylene, Y is selected from oxygen, $>NR^{10}$, wherein $R^{10}$ is hydrogen or alkyl of one to four carbon atoms, and $$-S-\overset{(O)_n}{\phantom{S}},$$

where n=0, 1 or 2, $L^3$ is selected from alkylene of one to three carbon atoms, propenylene, propynylene, , and , where Q is defined above and m=1, 2, or 3, $R^3$ is selected from hydrogen, alkyl of one to four carbon atoms, alkenyl of two to six carbon atoms, and alkynyl or two to six carbon atoms. $R^4$ and $R^5$ are independently selected from hydrogen, alkyl of one to four carbon atoms, alkenyl of two to six carbon atoms, and alkynyl or two to six carbon atoms.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure —NHR' wherein R' is alkyl as previously defined. Example of alkylamino include methylamino, ethylamino, iso-propylamino, and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, isopropylaminocarbonyl, and the like.

The term "alkanoyl" refers to an alkyl group, as defined above, attached to the parent molecular moiety through a carbonyl group. Alkanoyl groups are exemplified by formyl, acetyl, butanoyl, and the like.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxycarbonyl" represents an ester group; i.e. an alkoxy group attached to the parent molecular moiety through a carbonyl group. Representative alkoxycarbonyl groups include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The terms "alkenyl" and "alkynyl" refer to monovalent hydrocarbon groups having, respectively one carbon-carbon double or triple bond, and can be thought of as derived from an alkene or alkyne by removal of a single hydrogen atom.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "aminoalkyl" denotes an $-NH_2$ group attached to the parent molecular moiety through an alkylene group. Representative aminoalkyl groups include 2-amino-1-ethylene, 3-amino-1-propylene, 2-amino-1-propylene, and the like.

The term "carboxyalkyl" denotes a $-CO_2H$ group attached to the parent molecular moiety through an alkylene group. Representative carboxyalkyl groups include, 1-carboxyethyl, 2-carboxyethyl, 1-carboxypropyl, and the like.

The term "(alkoxycarbonyl)alkyl" denotes an alkoxycarbonyl group, as defined above, attached to the parent molecular moiety through an alkylene group. Representative (alkoxycarbonyl)alkyl groups include ethoxycarbonylmethyl, ethoxycarbonylethyl, methoxycarbonylpropyl, and the like.

The term "(alkylaminocarbonyl)alkyl" denotes an alkylamino-carbonyl group, as defined above, attached to the parent molecular moiety through an alkylene group. Examples of (alkylaminocarbonyl)alkyl groups include methylaminocarbonylmethyl, methylaminocarbonyl-propyl, isopropylaminocarbonylmethyl, and the like.

The term "alkenylene" denotes a divalent group derived from a straight or branched chain hydrocarbon containing at least one carbon-carbon double bond. Examples of alkenylene include $-CH=CH-$, $-CH_2CH=CH-$, $-C(CH_3)=CH-$, $-CH_2CH=CHCH_2-$, and the like.

Compounds of the present invention may exhibit stereoisomerism by virtue of the presence of one or more asymmetric or chiral centers in the compounds.

The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

Compounds contemplated as falling within the scope of the present invention include, but are not limited to:
4-[3-(4-(N',N'-dimethylaminocarbonyl-N-methylamino)benzyloxy)-trans-prop-1-enyl]-4-methoxytetrahydropyran,
4-[3-(4-(N-acetyl-N-methylamino)benzyloxy)-trans-prop-1-enyl]-4-methoxytetrahydropyran,
4-[3-(4-(N"N'-dimethylaminocarbonyl-N-methylamino)benzyloxy)-prop-1-ynyl]-4-methoxytetrahydropyran,
4-[3-(4-(N-acetyl-N-methylamino)benzyloxy)prop-1-ynyl]-4-methoxytetrahydropyran,
4-[3-(4-(N',N'-dimethylaminocarbonyl-N-methylamino)benzyloxy)-prop-1-yl]-4-methoxytetrahydropyran,
4-[3-(3-(4-(N',N'-dimethylaminocarbonyl-N-methylamino)phenyl)prop-2-ynyloxy)-trans-prop-1-enyl]-4-methoxytetrahydropyran,
4-[3-(3-(4-(N-acetyl-N-methylamino)phenyl)prop-2-ynyloxy)-trans -prop-1-enyl]-4-methoxytetrahydropyran,
4-[3-(3-(4-(N',N'-dimethylaminocarbonyl-N-methylamino)phenyl) -trans-prop-2-enyloxy)-trans-prop-1-enyl]-4-methoxytetrahydropyran,
4-[3-(3-(4-(N',N'-dimethylaminocarbonyl-N-methylamino)phenyl)prop-2-ynyloxy)prop-1-ynyl]-4-methoxytetrahydropyran,
4-[3-(3-(4-(N-acetyl-N-methylamino)phenyl)prop-2-ynyloxy)prop-1ynyl]-4-methoxytetrahydropyran,
4-[3-(4-(N-(1 -piperidinylcarbonyl)-N-methylamino)-benzyloxy)-trans -prop-1-enyl]-4-methoxytetrahydropyran,
4-[3-(4-(N-(4-morpholinocarbonyl)-N-methylamino)-benzyloxy)-trans -prop-1-enyl]-4-methoxytetrahydropyran,
4-[3-(4-(N-(4-thiomorpholinocarbonyl)-N-methylamino)benzyloxy) -trans-prop-1-enyl]-4-methoxytetrahydropyran,
4-[3-(4-(N-(1-piperazinylcarbonyl)-N-methylamino)-benzyloxy)-trans -prop-1-enyl]-4-methoxytetrahydropyran,
4-[3-(4-((N'-(3-bromoprop-1-yl)aminocarbonyl)-N-methylamino) benzyloxy)-trans-prop-1-enyl]-4-methoxytetrahydropyran,
4-[3-(4-((N'-(3-aminoprop-1-yl)aminocarbonyl)-N-methylamino) benzyloxy)-trans- prop-1-enyl]-4-methoxytetrahydropyran,
4-[3-(4-((N'-(3-hydroxyprop-1-yl)aminocarbonyl)-N-methylamino) benzyloxy)-trans-prop-1-enyl]-4-methoxytetrahydropyran,
4-[3-(4-((3-ethoxycarbonylprop-1-yl)aminocarbonyl)-N-methylamino) benzyloxy)-trans-prop-1-enyl]-4-methoxytetrahydropyran,
4-[3-(4-((3-carboxyprop-1-yl)aminocarbonyl)-N-methylamino) benzyloxy)-trans-prop-1-enyl]-4-methoxytetrahydropyran, and
4-[3-(4-((3-N'-methylaminocarbonylprop-1-yl)aminocarbonyl)-N -methylamino)benzyloxy)-trans-prop-1-enyl]-4-methoxytetrahydropyran,
4-[3-(4-((N'-(3-bromoprop-1-yl)-N'-methylaminocarbonyl )-N-methylamino) benzyloxy)-trans-prop-1-enyl]-4-methoxytetrahydropyran,
4-[3-(4-((N'-(3-aminoprop-1-yl)-N'-methylaminocarbonyl)-N-methylamino) 2-benzyloxy)-trans-prop-1-enyl]-4-methoxytetrahydropyran,
4-[3-(4-((N '-(3-hydroxyprop-1-yl)-N'-methylaminocarbonyl)-N-methylamino)benzyloxy) -trans-prop-1-enyl]-4-methoxytetrahydropyran,
4-[3-(4-((3-ethoxycarbonylprop-1-yl)-N'-methylaminocarbonyl)-N-methylamino) benzyloxy)-trans-prop-1-enyl]-4-methoxytetrahydropyran,
4-[3-(4-((3-carboxyprop-1-yl)-N'-methylaminocarbonyl)-N-methylamino) benzyloxy)-trans-prop-1-enyl ]-4-methoxytetrahydropyran, and
4-[3-(4-((3-N'-methylaminocarbonylprop-1-yl)-N'-methylaminocarbonyl)-N -methylamino)benzyloxy)-trans-prop-1-enyl]-4-methoxytetrahydropyran.

Preferred compounds of this invention have the structure

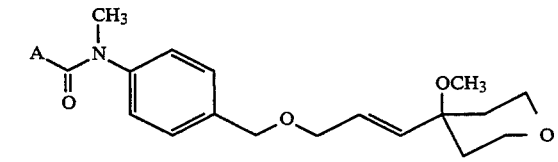

where A is methyl or -NR5R6 where $R^5$ and $R^6$ are defined above.

Examples of preferred compounds include, but are not limited to:
4-[3-(4-(N',N'-dimethylaminocarbonyl-N-methylamino)benzyloxy) -trans-prop-1 -enyl]-4-methoxytetrahydropyran,
4-[3-(4-((N'-(3-bromoprop-1-yl)-N'-methylaminocarbonyl)-N -methylamino)-benzyloxy)-trans-prop-1-enyl]-4-methoxy-tetrahydropyran,
4-[3-(4-((N'-(3- aminoprop-1-yl)-N'-methylaminocarbonyl)-N -methylamino)benzyloxy)-trans-prop-1-enyl]-4-methoxytetrahydropyran,
4-[3-(4-((N'-(3-hydroxyprop-1-yl)-N'-methylaminocarbonyl)-N -methylamino)-benzyloxy)-trans-prop-1-enyl]-4-methoxytetrahydropyran,
4-[3-(4-((N'-(3-ethoxycarbonylprop-1-yl)-N'-methylaminocarbonyl)-N -methyllamino)benzyloxy)-trans-prop-1-enyl]-4-methoxytetrahydropyran,
4-[3-(4-((N'-(3-carboxyprop-1-yl)-N'-methylaminocarbonyl)-N -methylamino)-benzyloxy)-trans-prop-1-enyl]-4-methoxytetrahydropyran, and
4-[3-(4-((N'-(3-N"-methylaminocarbonylprop-1-yl) methylaminocarbonyl)-N-methylamino)benzyloxy)- trans-prop-1-enyl]-4methoxytetrahydropyran,
or a pharmaceutically acceptable salt thereof.

Particularly preferred compounds of the present invention are 4-[3-(4-(N',N'-dimethyl-aminocarbonyl-N-methylamino)benzyloxy)-trans-prop-1-enyl]-4methoxytetrahydropyran, cis-2-methyl-4-[3-(4-((N'-(3-N"-methylaminocarbonylprop-1-yl)methylaminocarbonyl)-N-methylamino)benzyloxy) -trans-prop-1-enyl]-4-methoxytetrahydropyran, and trans-2-methy-4-[3-(4-((N'-(3-N"-methylaminocarbonylprop-1-yl)methylaminocarbonyl)-N -methylamino)benzyloxy)-trans-prop-1-enyl]-4-methoxytetrahydropyran
or a pharmaceutically acceptable salt thereof.

Lipoxygenase Inhibition Determination

Inhibition of leukotriene biosynthesis was evaluated in an assay, involving calcium ionophore-induced $LTB_4$ biosynthesis expressed human whole blood.

Human heparinized whole blood was preincubated with test compounds or vehicle for 15 min at 37° C. followed by calcium ionophore A23187 challenge (final concentration of 8.3 µM) and the reaction terminated after 30 min by adding two volumes of methanol containing prostaglandin $B_2$ as an internal recovery standard. The methanol extract was analyzed for $LTB_4$ using a commercially available radioimmunoassay. Employing this screening test, it was found that the compounds of this invention inhibit leukotriene biosynthesis.

Pharmaceutical Compositions

The present invention also provides pharmaceutical compositions which comprise compounds of the present invention formulated together with one or more non-toxic pharmaceutically acceptable carders. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarficular injection and infusion.

Pharmaceutical compositions of this invention for parenteral injection comprise pharmaceutically acceptable sterile aqueous or nonaqueous solutions, dispersions, a0 suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate mid gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinyl-pyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonitc clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymefic substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonitc, agars agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, is Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carder and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of this Invention

The compounds of this invention are prepared by a variety of synthetic routes. Representative procedures are outlined as follows, in which it should be understood that $L^1$, $R^1$, $R^2$, $R^3$, $R^4$, $R^5$, $R^6$, $R^7$, $R^8$, and W are as identified above.

A general route to the compounds of this invention is shown in Scheme 1. The magnesium salt of 0-TItP propargyl alcohol is condensed with tetrahydropyran-4-one to give tertiary alcohol 1. Alkenol 3 is prepared by reduction of 1 to the trans olefin 2 with a suitable reducing agent, preferably Red-Al (sodium bis(2-methoxyethoxy)aluminum), followed by alkylation with NaH and $R^3X$, and deprotection with pyridinium p-toluenesulfonate in methanol. Alkynol 5 is prepared by alkylation and deprotection of 1 as described above. Reduction of 5 with Red-Al provides another route to alkenol 3.

Alkylation of 5 by treatment with NaH and $ArCH_2X$ provides the alkynyl compound 6. Alternatively, 6 is prepared by treatment of $ArCH_2OH$ with NaH and iodide 7. Iodide 7 is prepared by conversion of 5 to the mesylate as described by Crossland and Servis, J. Org. Chem., 35, 3195–3196 (1970), and treatment of the mesylate with NaI. Alkenyl compound 8 is prepared by either route described for the preparation of 6.

Hydrogenation of either 6 or 8, preferably cayalyzed with palladium on barium carbonate poisoned with lead gives saturated compound 9.

Scheme 1

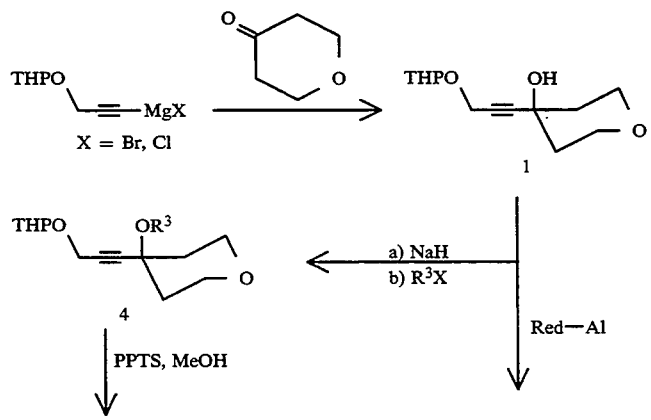

Scheme 1
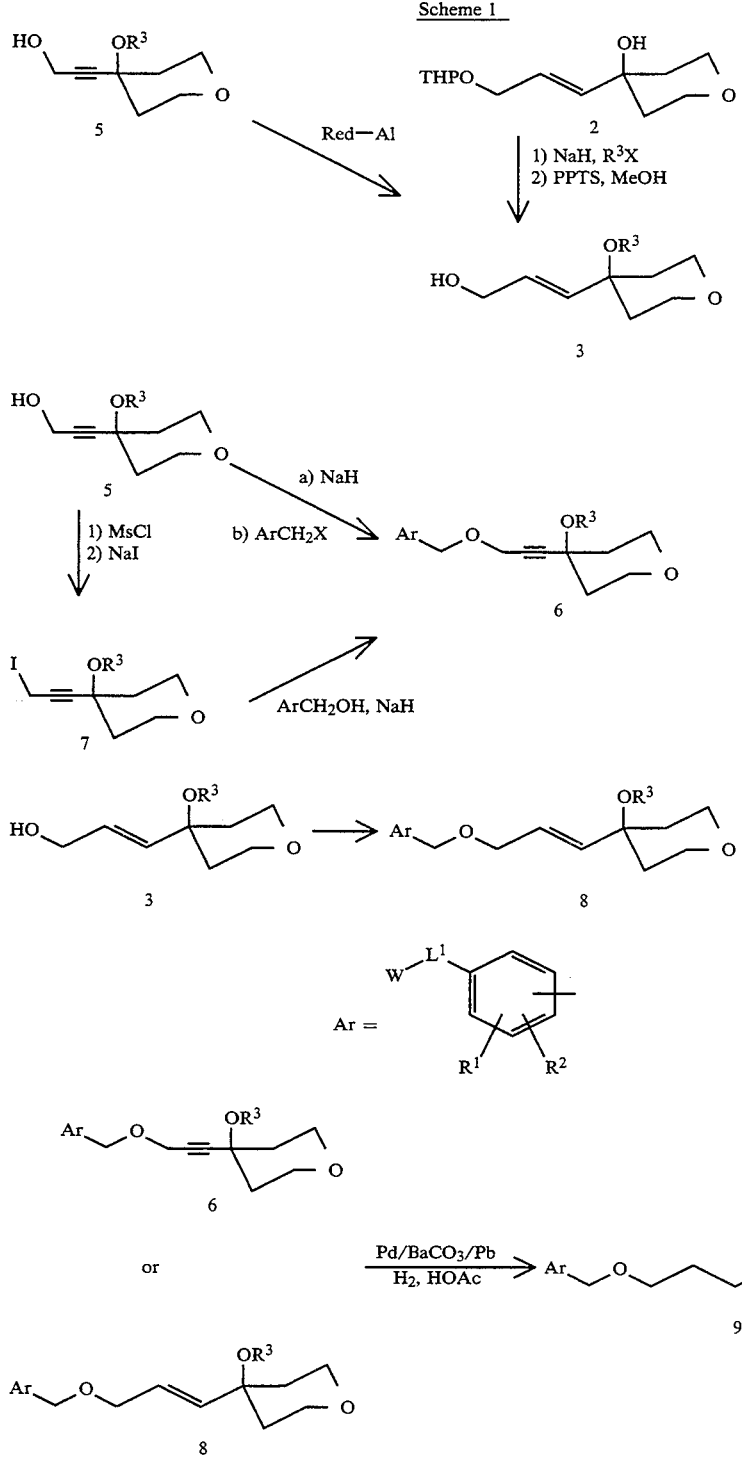
The preparation of compounds in which Y is S is shown in Scheme 2. Iodide 10 is prepared as described above. Displacement with the desired aryl thiolate forms 11. Arylmethylthio compound 12 is prepared according to the method of compound 11, except arylmethyl thiol is substituted for aryl thiol.
Scheme 2
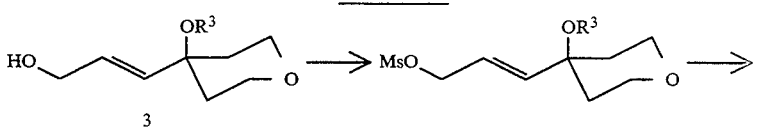

Scheme 2

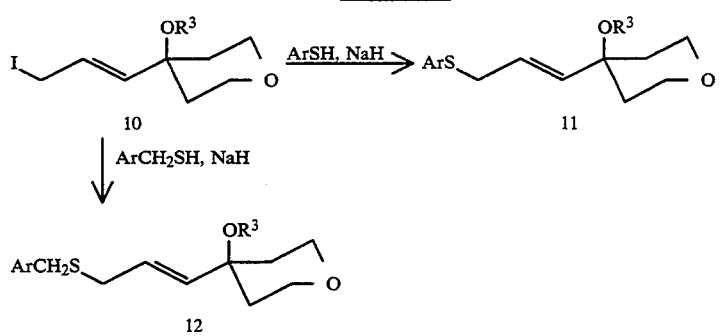

The preparation of α,β-unsaturated ketone derivatives is shown in Scheme 3. Primary alcohol 12 is oxidized to carboxylic acid 13 by treatment with a suitable oxidizing agent, preferably Jones Reagent. The carboxylic acid is converted to the acid chloride 14, by treatment with oxalyl chloride. Amide 15 is prepared by treatment of the acid chloride with the desired arymethylamine in the presence of a suitable base, preferably triethylamine.

Scheme 3

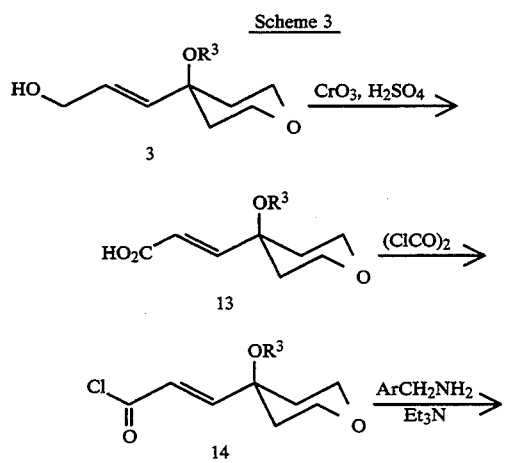

-continued
Scheme 3

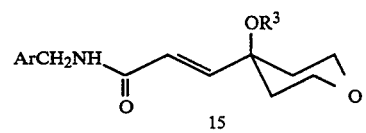

The preparation of compounds where $R^6$ is alkyl is shown in Scheme 4. The methyl ester of 4-aminobenzoic acid is treated allyloxycarbonyl chloride to produce 16. Reaction of 16 with sidum hydride and the desired alkyl halide, $R^6X$ yields 17 in which the nitrogen is substituted by the alkyl group derived from the alkyl halide. Treatment of 17 with the lithio salt of triethylborane ("superhydride"), followed by reaction with sodium hydride and 4-methoxy-4-(3-iodopropenyl)tetrahydropyran yields 18. Reaction of 18 with either palladium or rhodium removes the group from the nitrogen of the phenyl ring to yield 19 which can be reacted with trimethylsilylisocyanate to yield the N-R6-substituted urea, 20, or with alkyl lithium, followed by $R^7R^8NC(O)Cl$ to produce the N-R6, N',N'-$R^7$, $R^8$-substituted urea, 21.

Scheme 4

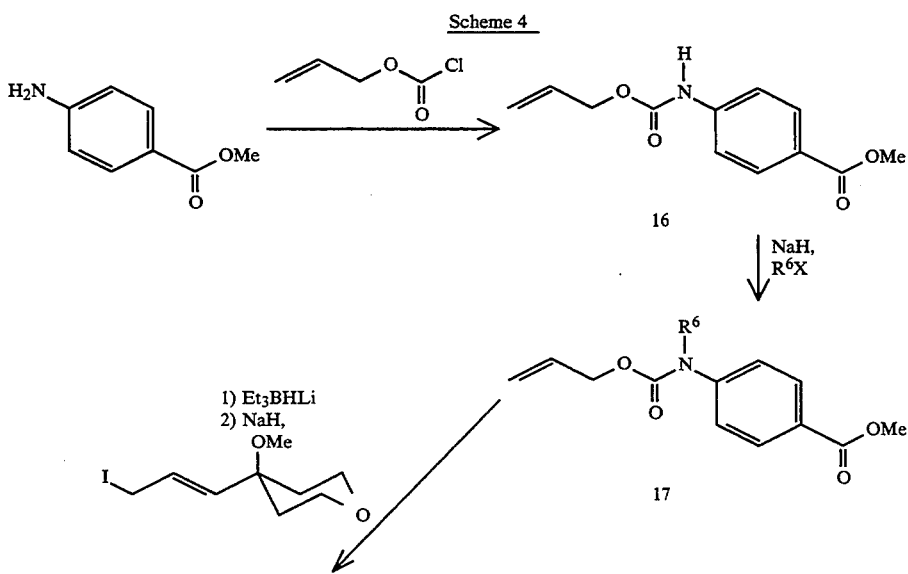

Scheme 4

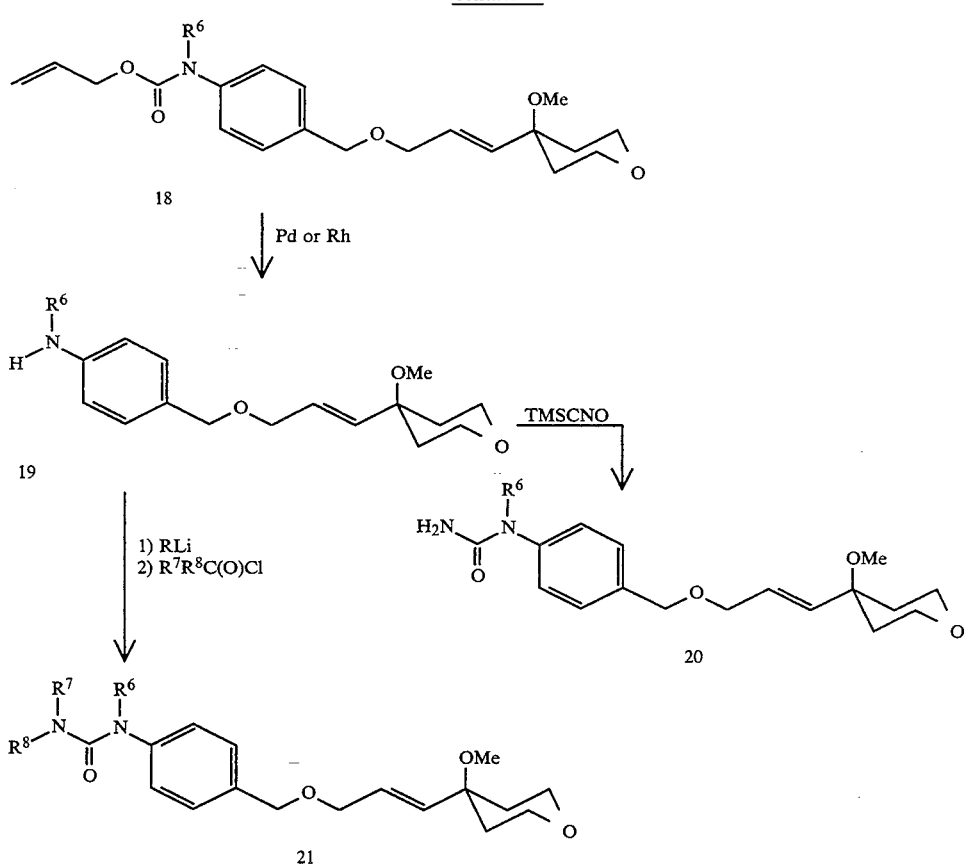

The preparation of the compounds of this invention where $R^8$ is haloalkyl or aminoalkyl is shown in Scheme 5. Amine 23, prepared as in scheme 4, is treated with the desired haloalkylisocyanate to form haloalkyl derivative 26. Conversion of 26 to azide 27, followed by reduction with 1,3-propanedithiol provides aminoalkyl derivative 28. Compounds in which $R^7$ is alkyl are prepared by alkylation of 27 followed by reduction with propanedithiol as described above.

Scheme 5

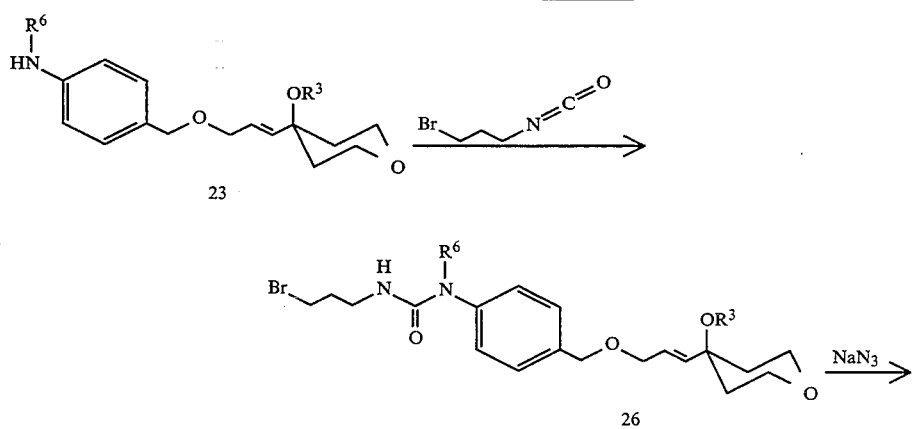

-continued
Scheme 5

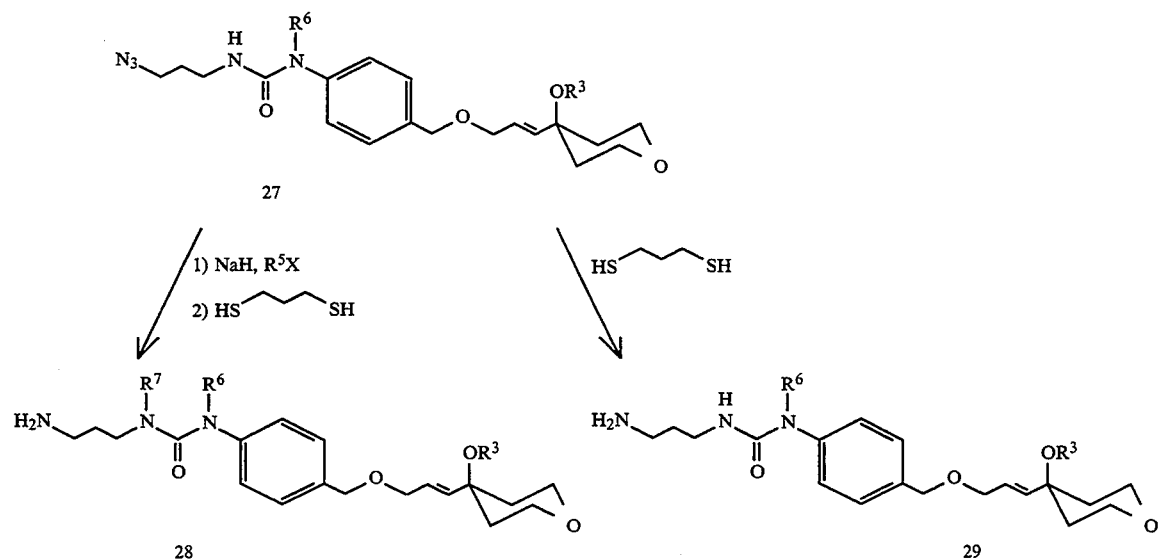

The preparation of the compounds of this invention where $R^6$ is hydroxyalkyl, carboxyalkyl, (alkoxycarbonyl)alkyl, or (alkylaminocarbonyl)-alkyl, is shown in Scheme 6. Amine 23 is treated with an alkoxy-carbonylalkylisocyanate to provide the alkoxycarbonylalkyl derivative 30, which is alkylated by treatment with NaH and $R^7X$. Hydrolysis of ester 31 provides (alkoxycarbonyl)alkyl derivative 32. Reduction of 32 with $BH_3$ provides the hydroxyalkyl compound 33. Alternatively, ester 31 may be reduced directly to 33 with lithium borohydride. The (alkylaminocarbonyl)-alkyl derivatives are prepared from ester 31 or acid 32 by standard synthetic methods.

Scheme 6

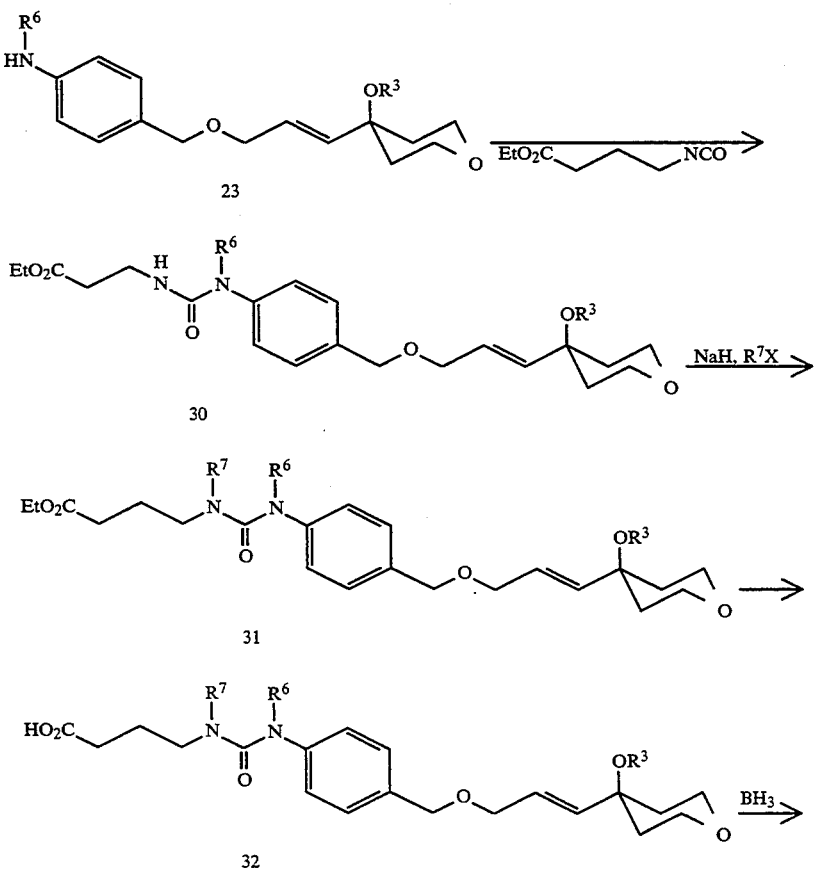

Scheme 6

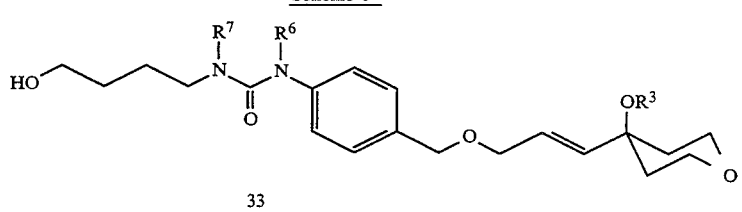

The preparation of the arylpropynyl, arylpropenyl, and arylpropyl ethers is shown in Scheme 7. 4-iodoaniline is converted to urea 34 by acylation with dimethylcarbamyl chloride, followed by alkylation with NaH and MeI. Coupling of 34 with propargyl alcohol provides propynol 35 which is converted to 36 as described in Scheme 1.

Treatment of alkynol 35 with Red-Al (sodium bis(2-methoxyethoxy)aluminum hydride) provides 37, which is coupled with iodide 10 as described in Scheme 1 to form 38. Catalytic hydrogenation of 38 provides saturated compound 39.

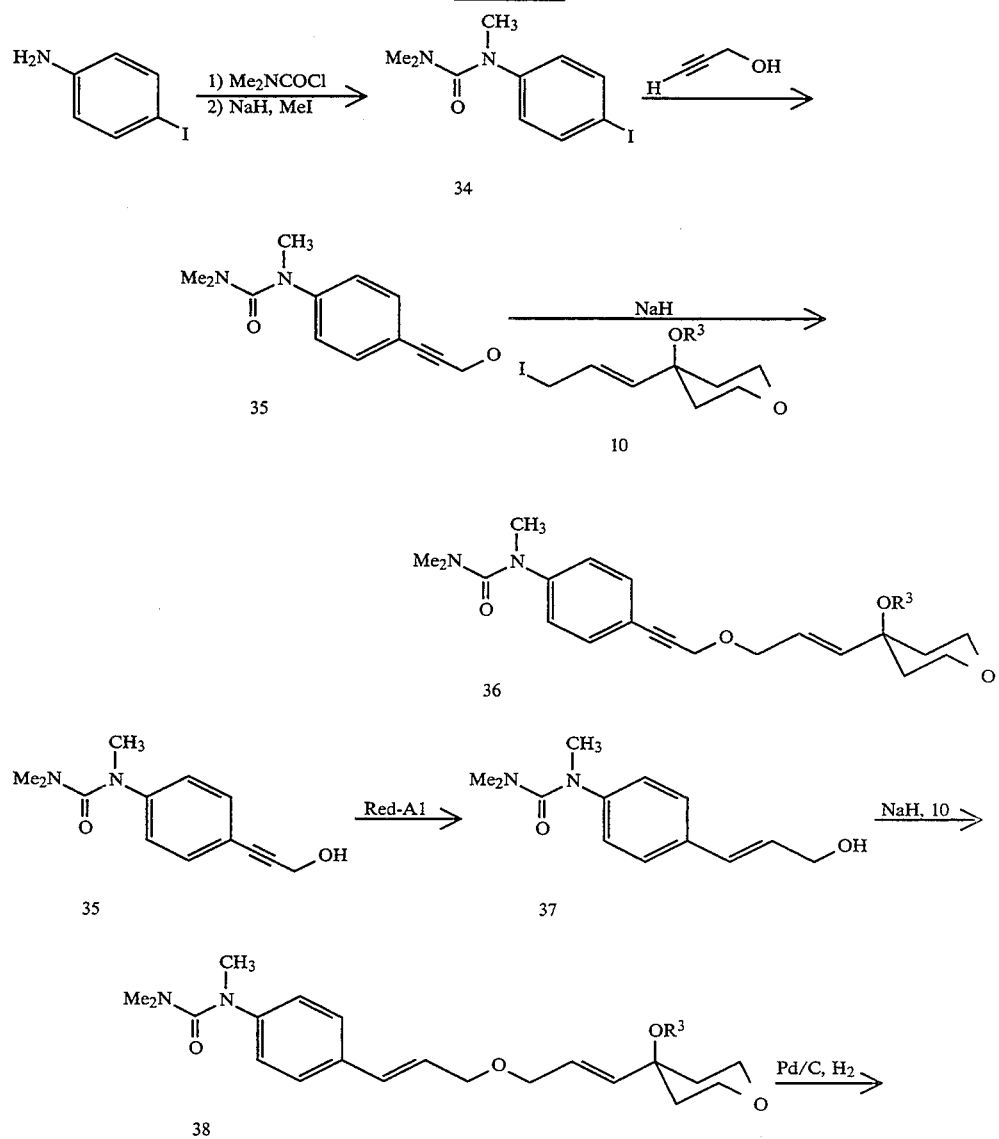

Scheme 7 -continued

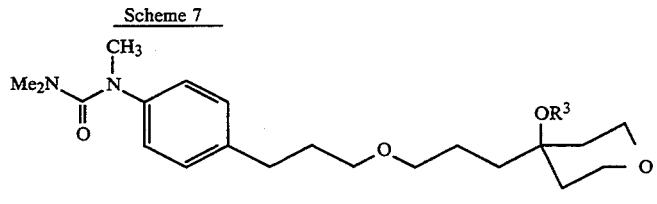

39

The foregoing may be better understood by the following examples, which are presented for illustration purposes only and are not intended to limit the scope of the invention.

EXAMPLE 1

Preparation of
4-[3-(4-(N',N'-dimethylaminocarbonyl-N-methylamino)-benzyloxy)
-trans-prop-1-enyl]-4-methoxytetrahydropyran

Step 1. Preparation of 4-hydroxy-4-[3-(tetrahydropyran-2-yloxy)-prop-1-ynyl]tetrahydropyran Tetrahydro-2-(2-propynyloxy)-2H-pyran (21 g, 150 mmol) was converted to the corresponding magnesium anion by deprotonation with ethyl magnesium bromide (75 mL of a 2M solution, 150 mmol) according to the method described in Org. Synth., 60:81–7 (1981). The resulting anion was cooled to −20° C. and tetrahydro-4H-pyran-4-one (14.8 g, 148 mmol) in dry THF (30 mL) was added dropwise and the resulting solution stirred for three hours. The reaction was quenched by addition of crushed ice and saturated aqueous ammonium chloride. The resulting two-layered mixture was extracted with ether (3×150 mL). The combined organic layers were dried (MgSO$_4$), filtered, and concentrated in vacuo. Purification by chromatography on silica gel (200 g, 20% ethyl acetate: hexanes) provided the desired acetylene tertiary alcohol (31.4 g, 88%).

Step 2. Preparation Of 4-hydroxy-4-[3-(tetrahydropyran-2-yloxy)-trans-prop-1-enyl]tetrahydropyran A solution of 4-hydroxy-4-[3-(tetrahydropyran-2-yloxy)-prop-1-ynyl]tetrahydropyran (10.8 g, 44.9 mmol),prepared as in step 1, in dry THF (100 mL) was cooled to −75 ° C., and Red-Al (20 mL of 3.4M solution in toluene, 68 mmol) was added under a dry argon atmosphere. The cooling bath was removed and the reaction was warmed to 0° C. and quenched by addition of crushed ice and saturated aqueous ammonium chloride. The resulting two-phase mixture was extracted with ethyl acetate (4×90 mL). The combined organic layers were dried (MgSO$_4$), filtered, and concentrated in vacuo. Purification by chromatography on silica gel (100 g, 10% ethyl acetate: hexanes) provided the trans olefin (3.71 g, 34 %) as a colorless oil.

Step 3. Preparation of 4-methoxy-4-[3-(tetrahydropyran-2-yloxy)-trans-prop-1enyl]tetrahydropyran The desired compound was prepared by addition of a solution in THF of 4-hydroxy-4-[3-(tetrahydropyran-2-yloxy)-trans-prop-1-enyl]tetrahydro-pyran, prepared as in step 2, to a suspension of NaH in THF, followed by alkylation of the resulting anion with methyl iodide.

Step 4. Preparation of 4-methoxy-4-(3-hydroxy-trans-prop-1-enyl)tetra-hydropyran The desired compound was prepared by treatment of a solution in methanol of 4-methoxy-4-[3-(tetrahydro-pyran-2-yloxy)-trans-prop-1-enyl]-tetrahydropyran, prepared as in step 3, with a catalytic amount of pyridinium p-toluenesulfonate (PPTS).

Step 5. Preparation of 4-methoxy-4-(3-methanesulfonyl-trans-prop-1-enyl)tetrahydropyran 4-methoxy-4-(3-hydroxy-trans-prop-1-enyl)tetrahydropyran, prepared as in step 4, was convened to the corresponding mesylate according to the method of Crossland and Servis, J. Org. Chem., 35, 3195–3196 (1970).

Step 6. Preparation of 4-methoxy-4-(3-iodo-trans-prop-1-enyl)-tetrahydropyran To a 0° C. solution in acetone of 4-methoxy-4-(3-methanesulfonyl-trans-prop-1-enyl)tetrahydropyran (730 mg, 2.92 mmol), prepared as in step 5, was added NaI (5.84 mmol, 875 mg). The cold bath was removed and the reaction mixture was stirred for 2 hours at ambient temperature. The reaction mixture was then concentrated and the residue partitioned between ether and H$_2$O. The organic phase was washed twice with brine, dried over MgSO$_4$, decolorized with activated carbon, filtered, through a pad of celite and concentrated in vacuo. The 4-methoxy-4-(3-iodo-trans -prop-1-enyl)tetrahydropyran (800 mg) so obtained was used without further purification.

Step 7. Preparation of Methyl 4-(N-methylamincarbonyl)amino-benzoate

A solution of methyl 4-aminobenzoate (15 g, 99 mmol), and methyl isocyanate (11.8 mL, 200 mmol) in toluene (400 mL) was heated at 100° C. under N$_2$ for 3 hours during which time a precipitate formed slowly. Additional methyl isocyanate (11.8 mL, 200 mmol) was added and heating was continued for 2 hours. The reaction mixture was cooled to 0° C. and filtered. The precipitate was washed with ether and vacuum-dried to give methyl 4-(N-methylaminocarbonyl)aminobenzoate as a colorless solid (17.5 g, 85% ).

Step 8. Preparation of Methyl 4-[(N',N'-dimethylaminocarbonyl)-N-methylamino]-benzoate To a 0° C. suspension of NaH (80% oil dispersion, 3.60 g, 120 mmol) in THF (200 mL) under N$_2$ was added a solution of methyl 4-(N -methylaminocarbonyl)aminobenzoate (10.0 g, 48 mmol), prepared as in step 1, in THF (40 mL). The reaction mixture was stirred at 0°

C. until gas evolution ceased, then the cold bath was removed and stirring was continued for 1.5 hours. A solution of iodomethane (6.6 mL, 106 mmol) in DMF (24 mL) was added and the reaction mixture was stirred for 72 hours at ambient temperature. NaH (2.0 g), and iodomethane (5.0 mL) were then added and the reaction mixture was stirred for an additional 2 hours. The reaction mixture was poured slowly into ice-water and the organics were stripped off in vacuo. The aqueous solution was extracted with ethyl acetate (10×). The combined organic layers were dried over MgSO$_4$, filtered, and concentrated. Pure methyl 4-[(N',N'-dimethylaminocarbonyl)-N-methylamino]benzoate (6.62 g, 58%) was obtained as a colorless oil which crystallized on standing after chromatography on silica gel (40%, then 50% ethyl acetate/hexanes). mp 71°–73° C.

Step 9. Preparation of 4-[(N', N'-dimethylaminocarbonyl)-N-methyl-amino]benzyl alcohol To a 0° C. solution of methyl 4-[(N',N'-dimethylaminocarbonyl)-N-methylamino]benzoate (1.50 g, 6.35 mmol), prepared as in step 2, in THF (11.4 mL) was added lithium triethylborohydride (1.0M solution in THF, 14 mmol). The reaction mixture was stirred for 1 hour. Water (3.0 mL) and H$_2$O$_2$ (30% aqueous solution, 5.0 mL) were added and the reaction mixture was stirred at 45° C. for 20 min. Aqueous HCL (6M, 8.0 mL) was added and the reaction mixture was stirred at reflux for 14 hours. The reaction mixture was cooled to ambient temperature and poured into ethyl acetate. The aqueous phase was extracted three times with ethyl acetate. The combined organic layers were dried over MgSO$_4$, filtered, and concentrated in vacuo. 4-[(N',N'-dimethylaminocarbonyl)-N-methylamino]benzyl alcohol (797 mg, 61%) was isolated as a colorless solid by chromatography on silica gel (ethyl acetate). mp 65°–66° C.

Step 10. Preparation of 4-[3,(4-(N',N'-dimelhylaminocarbonyl-N-methylamino) benzyloxy)-trans-prop-1-enyl]-4-methoxyethydropyran To a solution in DMF of 4-[(N', N'-dimethylaminocarbonyl)-N-methylamino]benzyl alcohol (128 mg, 0.615 mmol), prepared as in step 9, was added NaH (60% oil dispersion, 50 mg, 1.23 mmol), and the reaction mixture was stirred for 1 hour at ambient temperature. A solution in DMF of 4-methoxy-4-(3-iodo-trans -prop-1-enyl)tetrahydropyran (347 mg, 1.23 mmol) was added and the reaction mixture was stirred at ambient temperature for 18 hours. The reaction was quenched with saturated aqueous NH$_4$Cl solution and diluted with ethyl acetate. The organic phase was washed once with saturated aqueous NH$_4$Cl solution, twice with H$_2$O, once with brine, dried over MgSO$_4$, filtered, and concentrated in vacuo. 4-[3-(4-(N', N'-dimethylaminocarbonyl-N-methylamino)benzyloxy)-trans-prop-1-enyl]-4-methoxytetrahydropyran (77 mg, 31%) was obtained by chromatography on silica gel (80% ethyl acetate/hexanes). $^1$H NMR (300 MHz, CDCl$_3$) d 7.30 (2H, d, J=8.5 Hz), 7.03 (2H, d, J=8.5 Hz), 5.74 (1H, dr, J=16, 5.5, 5.5 Hz), 5.63 (1H, br d, J =16 Hz), 4.48 (2H, s), 4.49 (1H, dd, J=5.5, 1.5 Hz), 3.81 to 3.67 (4H, m), 3.22 (3H, s), 3.15 (3H, s), 2.70 (6H, s), 1.78 to 1.72 (4H, m). MS m/e 363 (M+H)$^+$, 380 (M+NH$_4$)$^+$. Analysis calc'd for: C, 66.27; H, 7.34; N, 7.73. Found: C, 66.28; H, 7.48; N, 7.34.

EXAMPLE 2

Preparation of 4-[3-(4-(N-acetyl-N-methylamino)benzyloxy)-trans-prop-1-enyl]-4-methoxytetrahydropyran

Step 1. Preparation of 4-(N-acetyl-N-methylamino)benzoic acid

To a solution of N-methyl-4-aminobenzoic acid (2.0 g, 13.2 mmol) in anhydrous pyridine (13.2 mL) was added acetic anhydride (1.4 mL, 14.5 mmol). The reaction was stirred at ambient temperature until TLC indicated complete reaction (~22 hours). The resultant solution was poured into ethyl acetate and the organic phase was washed (3×, 10% HCl; 1×, water; 1×, brine), dried (MgSO$_4$), filtered and concentrated in vacuo to provide the amide as a colorless solid. Recrystallization (ethyl acetate/hexane) afforded 4-(N-acetyl-N-methylamino)benzoic acid (2.15 g, 84.0%). $^1$H NMR (300 MHz, CDCl$_3$) d 8.18 (2H, br d, J=8.5 Hz), 7.33 (2H, br d, J=8.5 Hz), 3.33 (3H, s), 2.0 (3H, br s). MS m/e 194 (M+H)$^+$, 211 (M+NH$_4$)$^+$.

Step 2. Preparation of 4-(N-acetyl-N-methylamino)benzyl alcohol

An oven dried flask, under nitrogen flow, was charged with a stir bar, 4-(N -acetyl-N-methyl-amino)benzoic acid (1.0 g, 5.18 mmol), prepared as in step 7, anhydrous DME (10.3 mL), and anhydrous DMF (3.0 mL). The resulting solution was cooled to −20° C., and 4-methylmorpholine (0.60 mL, 5.4 mmol) and isobutyl chloroformate (0.70 mL, 5.4 mmol) were added sequentially via syringe. The reaction mixture was stirred under N$_2$ at −20° C. for 1 hour. The resultant yellow mixture was filtered and the precipitate washed with DME (2×, ~1 mL). The combined filtrate and washings were cooled to 0° C. and sodium borohydride (800 mg, 21.1 mmol) dissolved in water (2.0 mL) was added dropwise. The reaction was stirred at 0° C. for 15 min. and quenched with saturated aqueous ammonium chloride. The resulting mixture was partitioned between ethyl acetate and brine. The combined organic layers were dried (MgSO$_4$), filtered and concentrated in vacuo to give an oil. Purification by flash chromatography on silica gel (90% ethyl acetate/hexane) provided 4-(N-acetyl-N-methyl-amino)benzyl alcohol as a colorless oil which solidified on standing. Recrystallization from hexane provided the alcohol as a colorless solid (543.0 mg, 58.5%). $^1$H NMR (300 MHz, CDCl$_3$) d 7.45 (2H, d, J=8.5 Hz), 7.18 (2H, d, J=8.5 Hz), 4.75 (2H, s), 3.27 (3H, s), 1.90 (3H, br s). MS m/e 180 (M+H)$^+$, 197 (M+NH$_4$)$^+$.

Step 3. Preparation of 4-[3-(4-(N-acetyl-N-methylamino)benzyloxy)-trans-prop-1-enyl]-4-methoxytetrahydropyran The desired compound is prepared according to the method of Example 1, step 10, except substituting 4-(N-acetyl-N-methyl-amino)benzyl alcohol, prepared as in step 2, for 4-[(N',N'-dimethylaminocarbonyl)-N-methylamino]benzyl alcohol.

EXAMPLE 3

Preparation of
4-[3-(4-(N',N'-dimethylaminocarbonyl-N-methylamino)
benzyloxy)prop-1-ynyl]-4-methoxytetrahydropyran The desired compound is prepared according to the method of Example 1, steps 3–10, except substituting 4-hydroxy-4-[3-(tetrahydropyran-2-yloxy)prop-1-ynyl]tetrahydropyran, prepared as in Example 1, step 1, for 4-hydroxy-4-[3-(tetrahydropyran-2-yloxy)-trans-prop-1-enyl]tetrahydropyran

EXAMPLE 4

Preparation of
4-[3-(4-(N-acetyl-N-methylamino)benzyloxy)prop-1-ynyl]-4-methoxytetrahydropyran The desired compound is prepared according to the method of Example 3, except substituting 4-(N-acetyl-N-methyl-amino)benzyl alcohol, prepared as in Example 2, step 2, for 4-[(N',N'-dimethylamino-carbonyl)-N-methylamino]benzyl alcohol.

EXAMPLE 5

Preparation of
4-[3-(4-(N',N'-dimethylaminocarbonyl-N-methylamino)
benzyloxy)prop-1-yl]-4-methoxytetrahydropyran The desired compound is prepared by hydrogenation over palladium on calcium carbonate poisoned with lead, of 4-[3-(4-(N',N'-dimethylaminocarbonyl-N-methylamino)benzyloxy)-trans-prop-1-enyl]-4-methoxytetrahydropyran, which is prepared as described in Example 1.

EXAMPLE 6

Preparation of
4-[3-(3-(4-(N',N'-dimethylaminocarbonyl-N-methylamino)
phenyl)prop-2-ynyloxy)-trans-prop-1-enyl]-4-methoxytetrahydropyran

Step 1. Preparation of
4-(N',N'-dimethylaminocarbonylamino)-iodobenzene

A mixture of 4-iodoaniline (4.22 g, 19.3 mmol), triethylamine (2.78 mL), and dimethylcarbamoyl chloride (1.86 mL) in $CH_2Cl_2$ (100 mL) was stirred for 1 hour at ambient temperature and 2 hours at 80° C., during which time the $CH_2Cl_2$ evaporated. The residue was left standing at ambient temperature for 36 hours and was then partitioned between ethyl acetate (200 mL), and $H_2O$ (100 mL). The layers were separated and the organic phase was dried over $MgSO_4$, filtered, and concentrated in vacuo to give a solid. The crude solid was washed with 1:1 ethyl acetate/pentane to give 4-(N',N'-dimethylaminocarbonylamino)-iodobenzene (3.2 g, 55% yield). $^1H$ NMR (300 MHz, DMSO-d6) d 8.36 (1H, s), 7.54 (2H, dt, J=9.0, 1.5 Hz), 7.35 (2H, dr, J=9.0, 1.5 Hz), 2.91 (6H, s). MS rn/e 291 (M+H)+, 308 (M+NH4)+.

Step 2. Preparation of
4-(N',N'-dimethylaminocarbonyl-N-methylamino)iodobenzene The desired compound is prepared according to the method of Example 3, step 2, except substituting, 4-(N',N'-dimethylamino-carbonylamino)iodobenzene, prepared as in step 1, for 4-(N-methylaminocarbonyl)aminobenzoate. $^1H$ NMR (300 MHz, DMSO-d6) d 7.64 (2H, dt, J=9.0, 1.5 Hz), 7.86 (2H, dt, J=9.0, 1.5 Hz), 3.5 (3H, s), 2.65 (3H, s). MS m/e 305 (M+H)+, 322 (M+NH4)+.

Step 3. Preparation of
3-[4-(N',N'-dimethylaminocarbonyl-N-methyl-amino)phenyl]prop-2-yn-1-ol A mixture of 4-(N',N'-dimethylaminocarbonyl-N-methylamino)-iodobenzene (3.0 g, 9.9 mmol), propargyl alcohol (0.56 g, 10.0 mmol), CuI (0.82 g, 10.0 mmol), bis(triphenylphosphine)palladium(II)dichloride 0.18 g, 10.0 mmol) and triethylamine (30 mL), was stirred for 18 hours at ambient temperature. Saturated aqueous $NH_4Cl$ solution (50 mL) and $NH_4OH$ (10 mL) were then added and the reaction mixture was extracted with ethyl acetate. The organic phase was dried over $Na_2SO_4$, filtered, and concentrated in vacuo to give 3-[4-(N',N'-dimethylaminocarbonyl-N-methylamino)-phenyl]prop-1-ynol which was used without further purification. $^1H$ NMR (300 MHz, DMSO-d6) d 7.37 (2H, dr, J=9.0, 1.5 Hz), 7.00 (2H, dt, J=9.0, 1.5 Hz), 5.28 (1H, t, J=6.0 Hz), 4.28 (2H, d, J=6.0 Hz). MS m/e 233 (M+H)+, 250 (M+NH4)+.

Step 4. Preparation of
4-[3-(3-(4-(N',N'-dimethylaminocarbonyl-N-methylamino)phenyl)prop-2-ynyloxy)-trans-prop-1-enyl]-4-methoxy-tetrahydropyran The desired compound is prepared according to the method of Example 1, step 10, except substituting 3-[4-(N',N'-dimethylamino-carbonyl-N-methylamino)-phenyl]prop-2-yn-1-ol, prepared as in step 3, for 4-[(N',N'-dimethylaminocarbonyl)-N-methylamino]benzyl alcohol.

EXAMPLE 7

Preparation of
4-[3-(3-(4-(N-acetyl-N-methylamino)phenyl)prop-2-ynyl-oxy)-trans-prop-1-enyl]-4-methoxytetrahydropyran

Step 1. 4-(N-acetylamino)iodobenzene

The desired compound is prepared according to the method of Example 2, step 1, except substituting 4-iodoaniline for N-methyl-4-aminobenzoic acid.

Step 2. Preparation of
4-(N-acetyl-N-methylamino)iodobenzene

The desired compound is prepared according to the method of Example 3, step 2, except substituting, 4-(N-acetylamino)iodobenzene, prepared as in step 1, for 4-(N-methylaminocarbonyl)aminobenzoate

Step 3. Preparation of
4-[3-(3-(4-(N-acetyl-N-methylamino)phenyl)prop-2-ynyloxy)-trans-prop-1-enyl]-4-methoxytetrahydropyram The desired compound is prepared according to the method of Example 6, steps 3 and 4, except substituting 4-(N-acetyl-N-methylamino)iodobenzene, prepared as in step 2, for 4-(N',N'-dimethylaminocarbonyl-N-methylamino)iodobenzene.

EXAMPLE 8

Preparation of
4-[3-(3-(4-(N',N'-dimethylaminocarbonyl-N-methylamino)-phenyl)
-trans-prop-2-enyloxy)-trans-prop-1-enyl]-4-methoxytetrahydro-pyran

Step 1. Preparation of trans-3-[4-(N',N'-dimethylaminocarbonyl-N-methylamino)phenyl]prop-2-en-1-ol To a solution of 3-[4-(N',N'-dimethylaminocarbonyl-N-methylamino)phenyl]prop-2-yn-1-ol (0.35 g, 1.5 mmol), prepared in Example 6, step 3, in THF (10 mL) at −78° C. was added Red-Al (sodium bis(2-methoxyethoxy)aluminum hydride, 3.4 M in toluene, 0.44 mL, 1.5 mmol). The reaction mixture was stirred for 2 hours at −78° C., 2 hours at ambient temperature, and was then left standing at −20° C. for 18 hours. To the cold reaction mixture was added H2O (5 mL) and a few drops of dilute aqueous HCl. The reaction mixture was warmed to ambient temperature and extracted with ethyl acetate (2×50 mL). The organic phase was dried over MgSO4, filtered, and concentrated in vacuo to give trans-3-[4-(N',N'-dimethylaminocarbonyl-N-methylamino)-phenyl]-propen-1-ol (300 mg) which was used without further purification.

Step 2. Preparation of 4-[3-(3-(4-(N',N':dimethylaminocarbonyl-N-methylamino)phenyl)-trans-prop-2-enyloxy)-trans-prop-1-enyl]-4-methoxytetrahydropyran The desired compound is prepared according to the method of Example 6, step 4, except substituting trans-3-[4-(N',N'-dimethyl-aminocarbonyl-N-methylamino)-phenyl]prop-2-en-1-ol, prepared as in step 1, for 3-[4-(N',N'-dimethylaminocarbonyl-N-methylamino)-phenyl]-prop-2-yn- 1-ol.

EXAMPLE 9

Preparation of
4-[3-(3-(4-(N',N'-dimethylaminocarbonyl-N-methylamino)
-phenyl)prop-2-ynyloxy)prop-1-ynyl]-4-methoxytetrahydropyran The desired compound is prepared according to the method of Example 6, step 4, except substituting 4-methoxy-4-(3-hydroxyprop-1-ynyl)tetrahydropyran, prepared as in Example 3, for 4-methoxy-4-(3-hydroxy-trans-prop-1-enyl)tetrahydropyran.

EXAMPLE 10

Preparation of
4-[3-(3-(4-(N-acetyl-1-methylamino)phenyl)prop-2-ynyl-oxy)-prop-1-ynyl]-4-methoxytetrahydropyran The desired compound is prepared according to the method of Example 7, except substituting 4-methoxy-4-(3-hydroxyprop-1-ynyl)tetrahydropyran, prepared as in Example 3, for 4-methoxy-4-(3-hydroxy-trans-prop-1-enyl)tetrahydropyran.

The compounds represented in Table 1 are prepared as described in Scheme 3 and 4.

TABLE 1

Novel N-alkylurea inhibitors of 5-lipoxygenase

| Example | $R^6$ | $R^7$ | $R^8$ |
|---|---|---|---|
| 11 | Methyl | Hydrogen | Hydrogen |
| 12 | Methyl | Hydrogen | Methyl |
| 13 | Methyl | Hydrogen | Ethyl |
| 14 | Methyl | Hydrogen | Propyl |
| 15 | Methyl | Hydrogen | Butyl |
| 16 | Methyl | Ethyl | Methyl |
| 17 | Methyl | Propyl | Methyl |
| 18 | Methyl | Butyl | Methyl |
| 19 | Methyl | Ethyl | Ethyl |
| 20 | Methyl | Propyl | Propyl |
| 21 | Methyl | Butyl | Butyl |
| 22 | Methyl | Phenyl | Hydrogen |
| 23 | Methyl | Phenyl | Methyl |
| 24 | Methyl | piperidinyl | |
| 25 | Methyl | morpholinyl | |
| 26 | Methyl | thiomorpholinyl | |
| 27 | Methyl | 4-methylpiperazinyl | |
| 28 | Methyl | piperazinyl | |
| 29 | Ethyl | Hydrogen | Methyl |
| 30 | Ethyl | Methyl | Methyl |
| 31 | Propy | Hydrogen | Methyl |
| 32 | Propyl | Methyl | Methyl |
| 33 | Butyl | Hydrogen | Methyl |
| 34 | Butyl | Methyl | Methyl |

The compounds presented in Table 2 are prepared by the general synthetic method described in Reaction Scheme 5.

TABLE 2

Novel Haloalkyl-, Hydroxyalkyl-, Aminoalkyl-, (Alkoxycarbonyl)alkyl-, Carboxyalkyl-, and (Aminoalkylcarbonyl)alkylurea Derivatives of 5-Lipoxygenase.

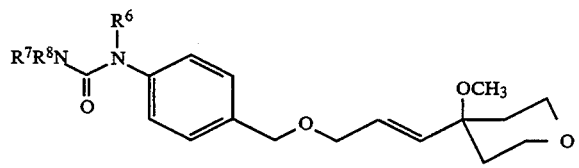

| Example | R⁶ | R⁸ | R⁷ |
|---|---|---|---|
| 35 | Methyl | Br~~~ | Hydrogen |
| 36 | Methyl | Br~~~ | Methyl |
| 37 | Methyl | H₂N~~~ | Hydrogen |
| 38 | Methyl | H₂N~~~ | Methyl |
| 39 | Methyl | HO~~~ | Hydrogen |
| 40 | Methyl | HO~~~ | Methyl |
| 41 | Methyl | HO-C(O)~~~ | Hydrogen |
| 42 | Methyl | HO-C(O)~~~ | Methyl |
| 43 | Methyl | EtO-C(O)~~~ | Hydrogen |
| 44 | Methyl | EtO-C(O)~~~ | Methyl |
| 45 | Methyl | CH₃-HN-C(O)~~~ | Hydrogen |
| 46 | Methyl | CH₃-HN-C(O)~~~ | Methyl |

The examples described above are merely illustrative of the invention and are not to be read as limiting the scope of the invention as it is defined by the appended claims.

We claim:

1. A compound having the structure

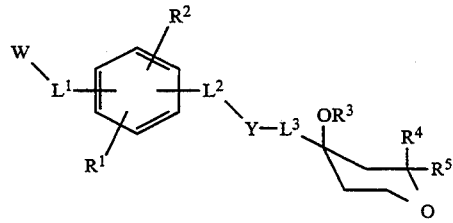

or a pharmaceutically acceptable salt thereof wherein
W is selected from the group consisting of

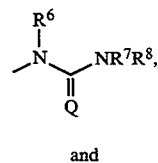 (a)

and

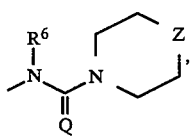 (b)

wherein
Q is oxygen,
R⁶ and R⁷ and R⁸ are independently selected from hydrogen and alkyl of one to four carbon atoms, provided that when L¹ is a valence bond, R⁶ is alkyl of one to four carbon atoms, and
Z is —CH₂—, oxygen, sulfur, or —NR⁹ where R⁹ is hydrogen or alkyl of one to four carbon atoms:
L¹ and L² are independently selected from a valence bond or alkylene of one to three carbon atoms, propenylene, and propymylene;
R¹ and R² are independently selected from the group consisting of
alkyl of one to four carbon atoms,
alkoxy of one to four carbon atoms,
haloalkyl of one to four carbon atoms,
halogen,
cyano,
amino,
alkylamino of one to four carbon atoms,
dialkylamino where the two alkyl groups are independently of one to four carbon atoms,
alkoxycarbonyl of two to four carbon atoms, and
dialkylaminocarbonyl where the alkyl portions are each of one to four carbon atoms;
Y is oxygen;
L³ is selected from the group consisting of
alkylene of one to three carbon atoms,
propenylene,
propynylene,

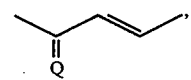

where
Q is as defined above, and

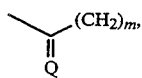

where Q is as defined above and m=1, 2, or 3;

R³ is selected from the group consisting of
hydrogen,
alkyl of one to four carbon atoms,
alkyenyl of three to six carbon atoms, and
alkynyl of three to six carbon atoms, and R⁴ and R⁵ are independently selected from the group consisting of
hydrogen,
alkyl of one to four carbon atoms,
alkyenyl of three to six carbon atoms, and
alkynyl of three to six carbon atoms.

2. A compound as defined in claim 1 having the structure

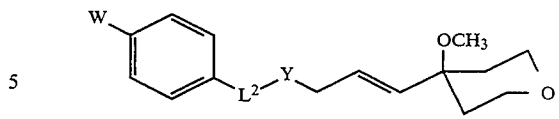

or a pharmaceutically acceptable salt thereof.

3. A compound or a pharmaceutically acceptable salt thereof as defined in claim 2 wherein L² is methylene.

4. The compound having the name 4-[3-(4-(N',N'-dimethylaminocarbonyl-N-methylamino)benzyloxy)-trans-prop-1-enyl]-4-methoxytetrahydropyran, or a pharmaceutically acceptable salt thereof.

5. A pharmaceutical composition comprising a therapeutically effective amount of a compound as defined by claim 1 in combination with a pharmaceutically acceptable carrier.

6. A method of inhibiting 5-lipoxygenase enzyme activity in a mammal in need of such treatment comprising administering a therapeutically effective amount of a compound as defined by claim 1.

* * * * *